United States Patent
Hwu et al.

(10) Patent No.: US 9,474,769 B2
(45) Date of Patent: Oct. 25, 2016

(54) METHODS OF TREATING CANCERS

(75) Inventors: Yeu-Kuang Hwu, Taipei (TW);
Tsung-Yeh Yang, Taipei (TW); Chi-Jen Liu, Taipei (TW); Chang-Hai Wang, Taipei (TW)

(73) Assignee: Yeu-Kuang Hwu, Taipei (TW)

( * ) Notice: Subject to any disclaimer, the term of this patent is extended or adjusted under 35 U.S.C. 154(b) by 963 days.

(21) Appl. No.: 12/028,026

(22) Filed: Feb. 8, 2008

(65) Prior Publication Data
US 2009/0202650 A1    Aug. 13, 2009

(51) Int. Cl.
*A61K 41/00* (2006.01)
*A61K 33/24* (2006.01)
*A61K 9/00* (2006.01)
*A61K 33/30* (2006.01)
*A61N 5/10* (2006.01)

(52) U.S. Cl.
CPC ............. *A61K 33/24* (2013.01); *A61K 9/0009* (2013.01); *A61K 33/30* (2013.01); *A61K 41/00* (2013.01); *A61N 5/10* (2013.01); *A61N 2005/1098* (2013.01)

(58) Field of Classification Search
CPC .. A61K 8/29; A61K 33/22; A61K 2800/413; A61K 6/046; C01G 23/047; C01G 23/003; C01P 2004/64; C01P 2004/84
See application file for complete search history.

(56) References Cited

U.S. PATENT DOCUMENTS

| | | | |
|---|---|---|---|
| 5,855,595 A * | 1/1999 | Fujishima et al. | 607/90 |
| 6,955,639 B2 * | 10/2005 | Hainfeld et al. | 600/1 |
| 7,094,860 B2 * | 8/2006 | Inaba et al. | 528/191 |
| 7,541,017 B2 * | 6/2009 | Bringley et al. | 424/1.29 |
| 2006/0264520 A1 * | 11/2006 | Sonezaki et al. | 516/90 |
| 2008/0261805 A1 * | 10/2008 | Kanehira et al. | 502/159 |

OTHER PUBLICATIONS

Cai et al., Cancer Res., 1992, 52:2346-2348.*
Sakthivel et al., Water Res., 2004, 38:3001-3008.*
Ichinose et al., Advanced Materials, 1998, 10(7): 535-539.*
Allemann et al., Int. J. Cancer., 1996, 66:821-824.*

* cited by examiner

*Primary Examiner* — Hong Sang
(74) *Attorney, Agent, or Firm* — McClure, Qualey & Rodack, LLP

(57) ABSTRACT

A method of treating cancer. The method includes introducing an effective amount of an oxidative catalyzing agent including titanium oxide, zinc oxide, zirconium oxide, tungsten oxide or tin oxide into a biological entity, and irradiating the biological entity with a ray. The oxidative catalyzing agent produces hydroxyl or hydrogen peroxide radicals after irradiation with the ray thereon.

4 Claims, 4 Drawing Sheets

METHODS OF TREATING CANCERS

BACKGROUND OF THE INVENTION

1. Field of the Invention

The invention relates to a therapeutic method, and in particular to a method of treating cancer.

2. Description of the Related Art

Malignant tumor or cancer continuously remains the leading cause of death in humans. Specifically, for people aged less than 85 years worldwide, its mortality rate has surpassed that of heart disease. Tumor diseases comprise of myeloma, leukemia, tumor of oral cavity, pharynx, digestive system, respiratory system, bones, joints, soft tissue, skin, breast, genital system, urinary system, eyes, orbits, nervous system or endocrine system. This statistic exhibits an increase in the incidence of cancer. Thus, development of a more effective therapy for cancer is urgent.

Various procedures such as surgical, radiological, thermotherapeutic and chemotherapeutic treatments have been developed and apply to cancer therapy. Specifically, cancer treatment employing photon-activation process provides a new option for cancer therapy. This approach could be roughly categorized into two groups: photodynamic therapy (PDT) and photo-catalytic therapy (PCT). PDT uses laser, or other light sources to activate a light-sensitive agent to destroy cancer cells. The photo-sensitive agent is normally a molecular agent or drug that makes cells more sensitive to light. Once in the body, the agent is attracted to cancer cells. When the light is directed at the area of the cancer, the agent is activated and the cancer cells are destroyed. The relevant materials, apparatus and methods utilized in PDT approach have been reported by various investigators (Y. Kawai, K. Endo and M. Yoshimura, "Apparatus for treatment of cancer with photodiode," U.S. Pat. No. 4,822,335; Fisher, G. Walter, Wachter, A. Eric and H. Graig, "Method for improved selectivity in photo-activation of molecular agents," U.S. Pat. No. 5,829,448).

PCT comprises another branch of optical methods to treat cancer. Photocatalysis, as the name suggests, refers to catalysis under light irradiation. The most important process is photo-induced charge separation and subsequent dark catalyses by the positive and negative charges. A. Fujishima and K. Honda firstly discovered in 1972 that UV light can induce water cleavage in the presence of TiO2, which was labeled as the first photocatalytic metal oxide material (A. Fujishima and K. Honda, Nature 238:37-38 (1972)). Besides $TiO_2$, more photocatalytic materials including both metal ($SnO_2$, ZnO, $ZrO_2$, CdO, $In_2O_3$, $WO_3$ and $SrTiO_3$ etc.) and metal chalcogenides (such as CdS, CdSe, $MoS_2$ and $WS_2$ etc.) have been intensively investigated. To further improve the photocatalytic efficiency, noble metals are doped to form composite photocatalytic materials (S. Vaidyanathan, E. W. Eduardo and V. K. Prashant, "Influence of Metal/Metal Ion Concentration on the Photocatalytic Activity of $TiO_2$—Au Composite Nanoparticles," Langmuir 19: 469-474 (2003); S. Vaidyanathan, E. W. Eduardo and V. K. Prashant, "Catalysis with $TiO_2$/Gold Nanocomposites. Effect of Metal Particle Size on the Fermi Level Equilibration," J. Am. Chem. Soc. 126: 4943-4950 (2004)).

Cancer treatments utilizing photocatalytic processes have been realized and practiced since the mid of 1980s. UV-illuminated $TiO_2$ colloids were first reported to possess strong oxidation power and kill tumor cells (A. Fujishima, J. ohtsuki, T. Yamashita, S. Hayakawa, Photomed. Photobiol. 8:45-46 (1986)). Subsequent experiments contributed to the optimization of catalytic conditions by investigating the influence of superoxide dismutase (R. Cai, K. Hashimoto, Y. Kubota, A. Fujishima, Chem. Lett. 427-430 (1992)) and the interactions, between $TiO_2$ and cells (R. Cai, H. Sakai, K. Hashimoto, Y. Kubota, A. Fujishima, Denki Kagaku 60:314-321 (1992); Y. Kubota, T. Shuin, C. Kawasaki, M. Hosaka, H. Kitamura, R. Cai, H. Sakai, K. Hashimoto, A. Fujishima, British Journal of Cancer 70:1107-1111 (1994)). Furthermore, some vivo experiments have also been conducted and confirmed remarkable cancer treatment efficacy (R. Cai, Y. Kubota, T. Shuin, H. Sakai, K. Hashimoto, A. Fujishima, Cancer Res. 52: 2345-2348 (1992); Y. Kubota, M. Hosaka, K. Hashimoto, A. Fujishima, Regional Cancer Treatment 8:192-197 (1995); A. Fujishima, T. N. Rao, D. A. Tryk, Journal of Photochem. Photobiol. C: 1: 1-21 (2000)).

Even with promising efficacy of this approach, three critical drawbacks limit its clinic applications: (1) the need for UV illumination which is not a biocompatible light source; (2) the limited penetration of UV light require optical fiber and additional surgical operation; (3) the photocatalytic treatment with titania nanoparticles is unsuitable for larger and irregular tumors.

Recently it has been demonstrated that ionization radiation such as gamma-rays could also trigger the photocatalytic process using $TiO_2$ nanoparticles as the model photocatalyst (N. Chitose, S. Ueta, S. Seino, T. A. Yamamoto, Chemosphere 50: 1007-1013(2003)). The radiation-induced photocatalytic effects of $TiO_2$ particles might find useful applications in environmental engineering. However, the usage of X-ray coupled with $TiO_2$ nanoparticles in terms of photocatalytic effects have not been investigated so far. The usage of X-rays which have the most widespread applications in medicine might provide a solution to the above mentioned deadlocks encountered in UV-activated photocatalytic effect.

BRIEF SUMMARY OF THE INVENTION

The invention provides a method of treating cancer, comprising introducing an effective amount of an oxidative catalyzing agent into a biological entity, and irradiating the biological entity with a ray.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawing, wherein.

DETAILED DESCRIPTION OF THE INVENTION

Figure 1:
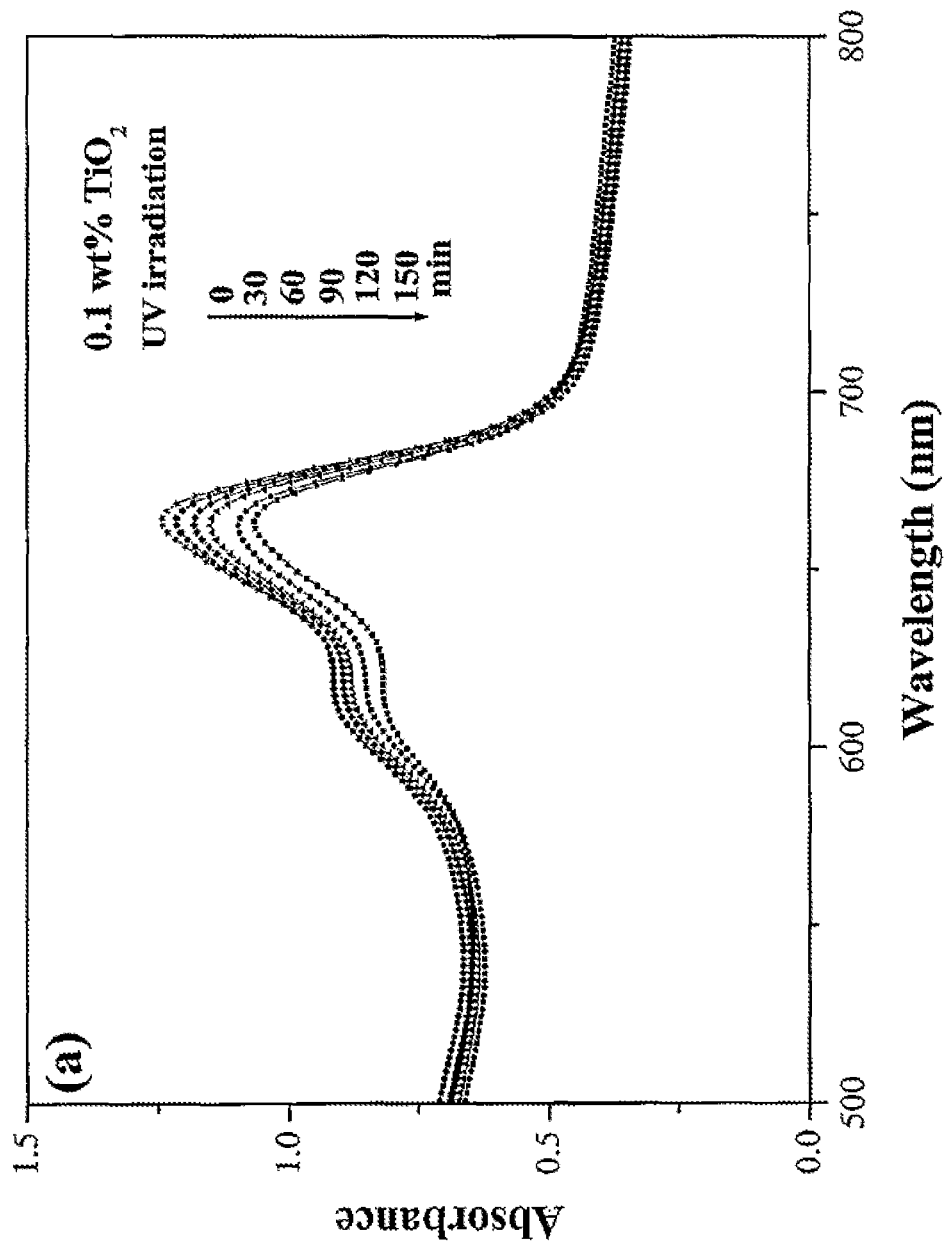
FIG. 1 shows various MB bleaching after UV and x-ray irradiation, respectively.

The following description is of the best-contemplated mode of carrying out the invention. This description is made for the purpose of illustrating the general principles of the invention and should not be taken in a limiting sense. The scope of the invention is best determined by reference to the appended claims.

The invention provides a method of treating cancer, comprising the following steps. An effective amount of an oxidative catalyzing agent is introduced into a biological entity. The biological entity is then irradiated with a ray.

The oxidative catalyzing agent may be a semiconductor nanoparticle having a diameter of about 10~100 nm, preferably 10-50 nm, and may comprise titanium oxide, zinc oxide, zirconium oxide, tungsten oxide or tin oxide.

The oxidative catalyzing agent may further be encapsulated by a surface layer material containing at least a hydroxyl group grafted thereon. The surface layer material may comprise synthetic polymers, peptides, polypeptides, antibodies or fragments thereof, nucleic acids, carbohydrate molecules, lipid molecules, drugs or synthetic molecules.

In addition, the oxidative catalyzing agent may be further modified by loading the transition metal on the surface of the semiconductor nanoparticle. The transition metal candidates may include gold, silver or platinum.

The biological entity may comprise plaques of blood vessels, mesangial tissues or cells, basement membrane of kidney, adipocytes, infected lung cells, infected red blood cells or bone tissues. The biological entity may also be a tumor such as solid tumor. The disclosed oxidative catalyzing agent can treat tumor of blood, oral cavity, pharynx, digestive system, respiratory system, bones, joints, soft tissues, skin, breast, genital system, urinary system, eyes, orbits, nervous system or endocrine system such as myeloma, leukemia, carcinomas, brain tumor, melanomas, lymphomas, plasmocytoma, sarcoma, glioma or thymoma.

The ray irradiated to the biological entity may comprise alpha ray, gamma ray, x-ray, proton beam, electron beam or neutron beam. After irradiating, the oxidative catalyzing agent may produce hydroxyl or hydrogen peroxide radicals.

In the invention, illuminated metal oxides (such as $TiO_2$, $SnO_2$, $ZnO$, $ZrO_2$ or $WO_3$) with strong oxidizing power are used to kill tumor cells. The metal oxide nanoparticles ranging from 10~100 nm are first catalyzed by synchrotron x-ray irradiation, producing hydroxyl or hydrogen peroxide radicals, causing oxidative damage and cancerous cell death. The singularity of the synchrotron x-ray in terms of deep penetration and ability to focus facilitates clinical diagnosis and eradication of tumor tissues. The invention may also be applied in bioimaging, drug delivery system or new cancer therapies.

Synchrotron x-ray irradiation provides super properties such as deep penetration and ability to focus. Furthermore, the high flux of high energy photons signifies a very efficient illumination light source.

Additionally, the titanium oxide nanoparticles prepared by sol-gel process are suitable for use in tumor cell treatment. Also, the influences of particle size and surface properties on the behavior of tumor cell can be clarified thereby.

Example 1

$TiO_2$ Nanoparticle Preparation 0.01 g of anatase $TiO_2$ (Titanium Oxide P25, Degussa Inc. NJ. US) was slowly added to 10 ml deionized water in flask to prepare well mixed $TiO_2$ nanosol with constant stirring.

Methylene Blue Bleaching

Methylene Blue (MB) purchased from Riedel de Haën (Seelze, Germany). The procedure of the experiment included two parts, irradiation under the discharge lamp at different times (30 to 150 minutes), and irradiation by x-ray for 5 minutes. After each irradiation, to detect the remaining methylene blue the absorbance of the mixture was measured with a UV spectrometer. This is a standard method to measure the photocatalytic activity.

FIG. 1 shows background-normalized spectra after ultraviolet and X-ray exposures of different durations. As the exposure time increases, the 664 nm absorption peak intensity decreases, reflecting the degradation of methylene blue resulting from the photocatalytic effect. The results indicate that x-ray enhances higher reaction rate than UV light. X-ray exhibits excellent MB bleaching.

Example 2

$TiO_2$/Au Nanoparticles Preparation 0.01 g of anatase $TiO_2$ (Titanium Oxide P25, Degussa Inc. NJ. US) was slowly added to 10 ml deionized water in flask to prepare well mixed $TiO_2$ nanosol with constant stirring. The well mixed aqueous solution containing 0.02M gold precursors (hydrogen tetrachloroaurate trihydrate, $HAuCl_4 \cdot 3H_2O$, Aldrich) with 0.1M NaOH were subsequently added to the $TiO_2$ nanosol while stirring vigorously to form $TiO_2$/Au sample solution. The prepared solution was then exposed to high flux of energetic X-ray photons to form the as-prepared $TiO_2$/Au.

In Vitro Observation of Cell Interaction with $TiO_2$ or $TiO_2$/Au Nanoparticles For TEM sample preparation, $1 \times 10^5$ mammary carcinoma EMT cells were seeded on 100 mm culture dish. After 24 hours, 0.5 mM anatase $TiO_2$ or $TiO_2$/Au nanoparticles was added to the culture media. After co-incubating for 48 hours, the cells with $TiO_2$ or $TiO_2$/Au nanoparticles were trypsinized, centrifuged, and washed with PBS/5% sucrose for at least three times to remove the remaining particles. Subsequently, the cells were fixed for 2 hours in 2.5% glutaraldehyde, and postfixed for 2 hours in 1% osmium tetroxide. Dehydration was achieved by 25%, 50%, 75%, 95%, and 100% ethanol. The samples were then infiltrated and embedded in 100% resin. Ultrathin sections prepared by an ultramicrotome were placed on 200-mesh copper grids for TEM measurement.

Figure 2A:
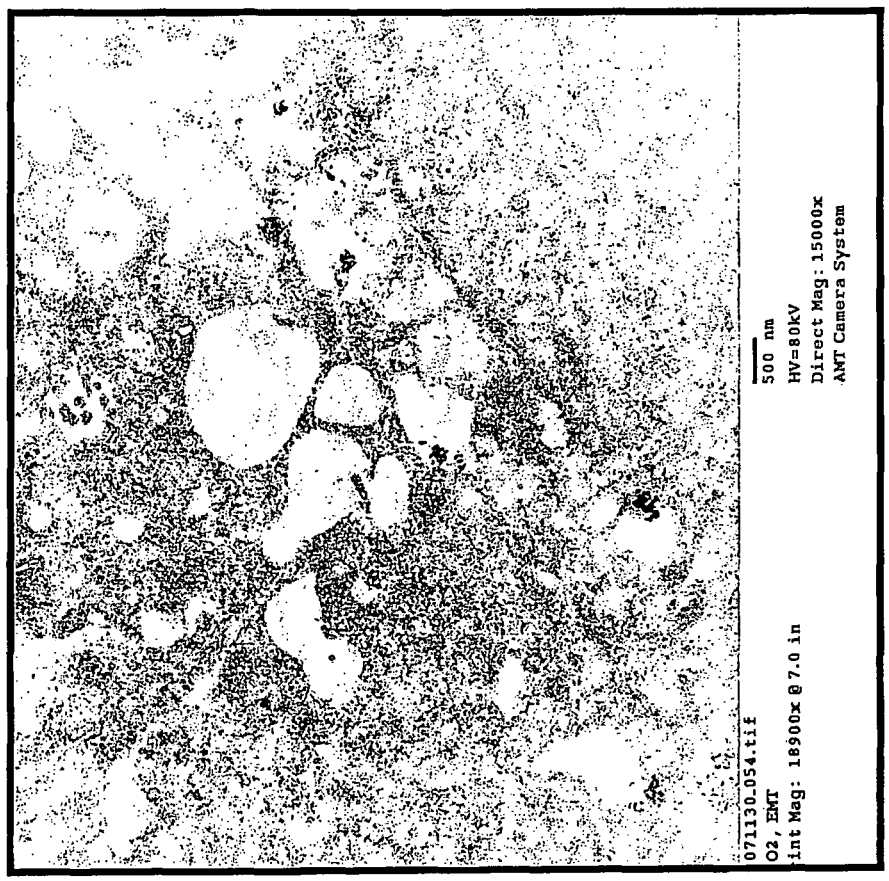
FIGS. 2 (a) and (b) show $TiO_2$ and $TiO_2$/Au nanoparticle internalization within EMT-6 cells.
Figure 2B:
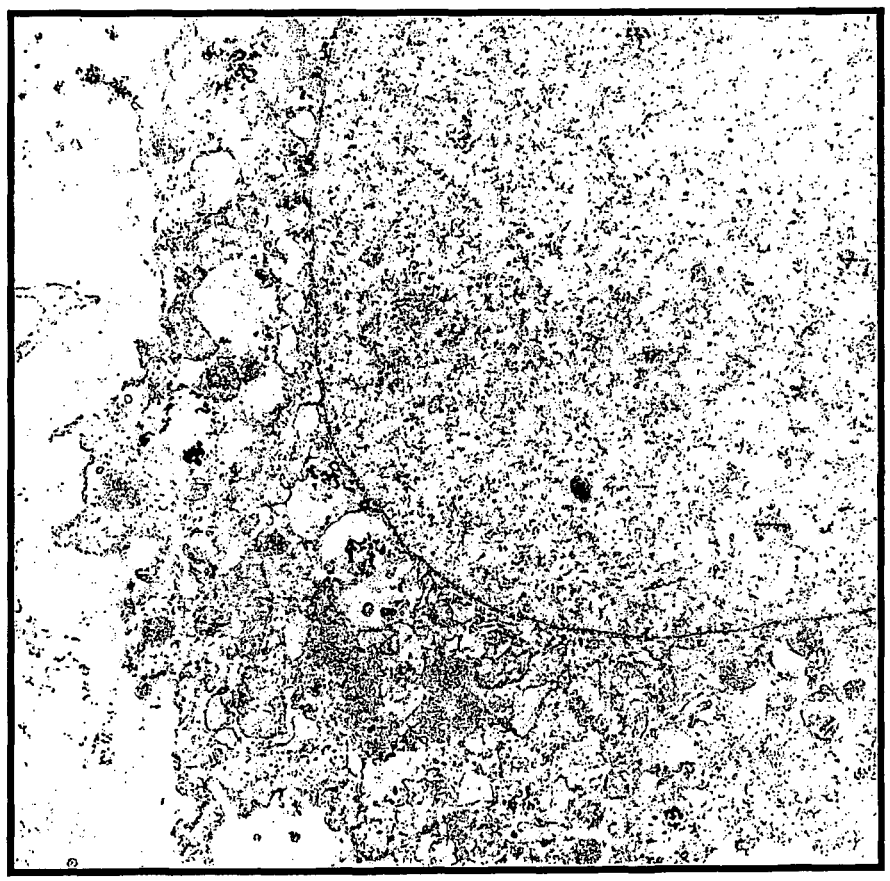

FIG. 2(a) and FIG. 2(b) show the evidence that a large amount of $TiO_2$ or $TiO_2$/Au nanoparticles were internalized in the cytoplasm of EMT-6 cells. The nanoparticles can indeed be clearly seen inside vesicles within the cytoplasm. No nanoparticles could be detected inside the cell nucleus, and most nanoparticles were agglomerated.

Example 3

In Vitro Cell Damage Study

For in vitro cell damage study, 750 mammary carcinoma EMT-6 cells were seeded on a 96-well culture dish. After 24 hours, 0.5 mM anatase $TiO_2$ or $TiO_2$/Au nanoparticles was added to the culture media. After co-incubating for 48 hours, synchrotron x-ray light source was introduced to perform the cell damage study. The exposure time of synchrotron x-ray was set at 5 min and the cell viability was examined by a standard cell viability test using MTT assay.

Figure 3:
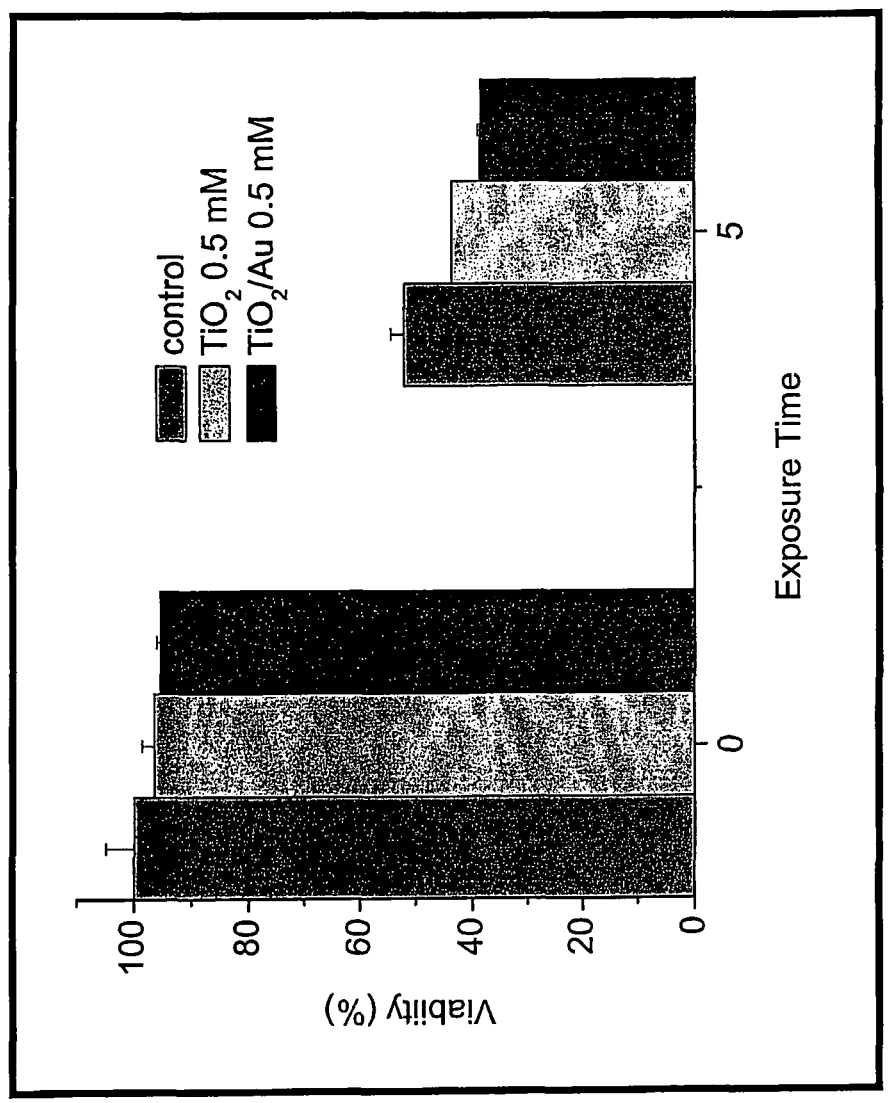
FIG. 3 shows viability of EMT-6 cells cultured with $TiO_2$ and $TiO_2$/Au nanoparticle at 48 hours after x-ray irradiation.

FIG. 3 indicated biocompatibility of anatase $TiO_2$ and $TiO_2$/Au nanoparticles up to 0.5 mM. Adding $TiO_2$ and $TiO_2$/Au nanoparticles indeed increased cytotoxicity after X-ray irradiation due to nanoparticle internalization within cells as shown in FIG. 2. The result also indicated that the degree of $TiO_2$/Au nanoparticle enabled enhancement effect on the suppression of the cell proliferation rate by x-ray irradiation is higher than pure $TiO_2$ nanoparticles.

In summary, X-rays is integrated with TiO$_2$ nanoparticles and apply for PCT. The invention demonstrates that: (1) compared with UV illumination conditions, X-ray induced photocatalytic effect of TiO$_2$ nanoparticles can be greatly enhanced; (2) under identical conditions, the immobilization of gold nanoparticles on TiO$_2$ further improve the photocatalytic efficacy; (3) in vitro studies indicate enhanced cell killing using nanoparticles under X-ray irradiation.

While the invention has been described by way of example and in terms of preferred embodiment, it is to be understood that the invention is not limited thereto. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method of treating cancer, comprising:
    introducing an effective amount of titanium oxide modified by loading gold on the surface of the titanium oxide encapsulated by a surface layer material comprising at least a hydroxyl group grafted thereon into a cancer; and
    irradiating the cancer with x-ray.

2. The method of treating cancer as claimed in claim 1, wherein the surface layer material comprises synthetic polymers, peptides, polypeptides, antibodies or binding fragments thereof, nucleic acids, carbohydrate molecules, lipid molecules, drugs or synthetic molecules.

3. The method of treating cancer as claimed in claim 1, wherein the cancer is a cancer of blood, oral cavity, pharynx, digestive system, respiratory system, bones, joints, soft tissues, skin, breast, genital system, urinary system, eyes, orbits, nervous system or endocrine system.

4. The method of treating cancer as claimed in claim 1, wherein the cancer is myeloma, leukemia, carcinomas, brain tumor, melanomas, lymphomas, plasmocytoma, sarcoma, glioma or thymoma.

* * * * *